United States Patent [19]

Kousai et al.

[11] Patent Number: 4,919,605
[45] Date of Patent: Apr. 24, 1990

[54] EXTRUSION APPARATUS FOR MOLDING GUIDING TUBE FOR MEDICAL INSTRUMENTS

[75] Inventors: Tadashi Kousai; Yousuke Moriuchi; Toshinobu Ishida, all of Fujinomiya, Japan

[73] Assignee: Terumo Kabushiki Kaisha, Tokyo, Japan

[21] Appl. No.: 269,727

[22] Filed: Nov. 9, 1988

Related U.S. Application Data

[62] Division of Ser. No. 48,675, May 11, 1987, Pat. No. 4,830,805.

[30] Foreign Application Priority Data

May 14, 1986 [JP] Japan ................................ 61-109922

[51] Int. Cl.⁵ ............................................. B29C 47/20
[52] U.S. Cl. ..................................... 425/467; 264/159; 425/382.4
[58] Field of Search ........................... 264/209.1–209.8, 264/159; 425/461–462, 465–467, 380, 382 R, 382.4

[56] References Cited

U.S. PATENT DOCUMENTS

| | | | |
|---|---|---|---|
| 1,184,254 | 5/1916 | McBean | 425/467 |
| 2,524,829 | 10/1950 | Perzel | 425/465 |
| 3,656,479 | 4/1972 | Huggins | 128/214.4 |
| 3,713,442 | 1/1972 | Walter | 128/214.4 |
| 3,899,283 | 8/1975 | Wallis | 425/467 |
| 4,054,136 | 10/1977 | von Zeppelin | 128/214.4 |
| 4,402,685 | 9/1983 | Bühler et al. | 604/164 |
| 4,451,256 | 5/1984 | Weikl et al. | 604/164 |

FOREIGN PATENT DOCUMENTS 51-47961  4/1976  Japan .................................. 425/467

*Primary Examiner*—Jeffery Thurlow
*Attorney, Agent, or Firm*—Frishauf, Holtz, Goodman & Woodward

[57] ABSTRACT

An extruder apparatus for molding a tube used for guiding a rod-like medical instrument into a living body. The resulting tubular body is made of a synthetic resin and has a longitudinal hollow portion to permit the passage of the rod-like medical instrument. The whole of the tubular body is formed to have a chemical uniformity, but at least one brittle portion such as a weld line is longitudinally formed over the entire length (or almost the entire length except the tip portion) of the tubular body. The brittle portion is formed by a die including a nozzle having a resin flow passageway of annular cross section. At least one baffle extends radially into the passageway for substantially temporarily splitting the flow which is then recombined to form the brittle portion.

2 Claims, 3 Drawing Sheets

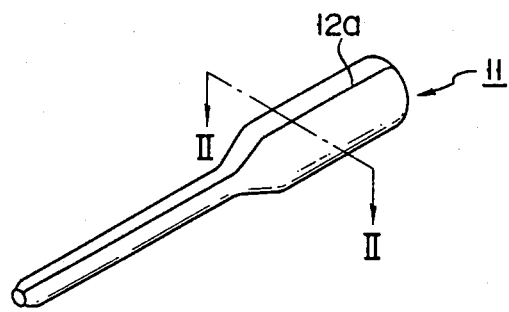
F I G. 1
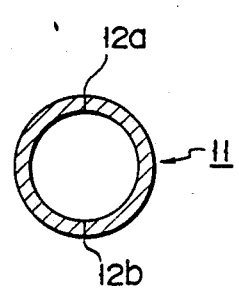
F I G. 2
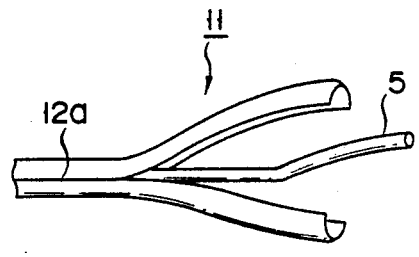
F I G. 3

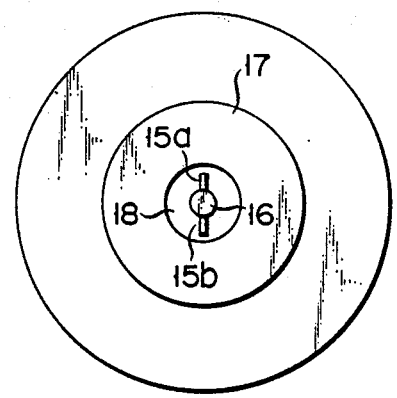
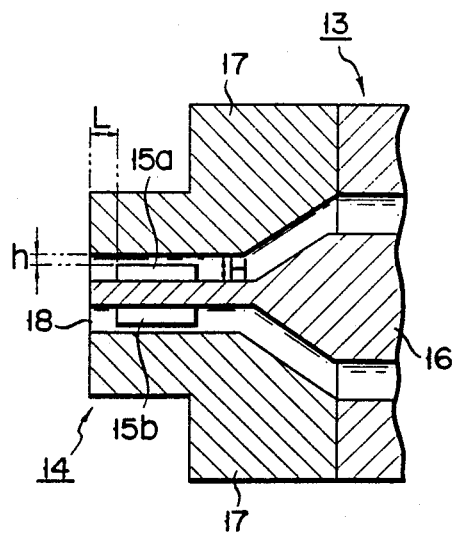
FIG. 4          FIG. 5
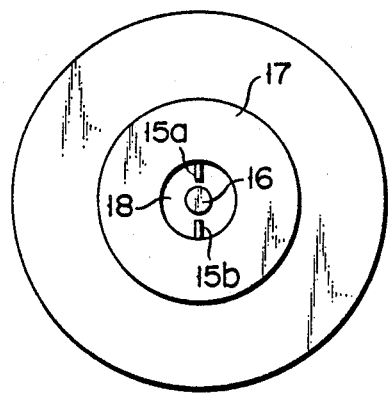
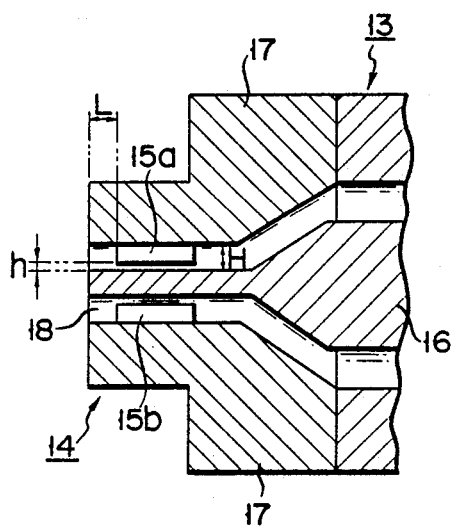
FIG. 6          FIG. 7

EXTRUSION APPARATUS FOR MOLDING GUIDING TUBE FOR MEDICAL INSTRUMENTS

This is a division of application Ser. No. 048,675, filed May 11, 1987, now U.S. Pat. No. 4,830,805, issued May 16, 1989.

BACKGROUND OF THE INVENTION

The present invention relates to a synthetic resin tube for guiding a rod-like medical instrument such as a catheter and a guide wire into, for example, a blood vessel and for keeping the medical instrument attached to the blood vessel.

A flexible tube of synthetic resin is generally used for guiding, for example, a catheter into a blood vessel and for keeping the catheter attached to the blood vessel. As shown in FIG. 8, a guiding tube 1 is mounted to a syringe 2 such that the tip of an inner needle 3 of the syringe 2 projects outward through the tip of the guiding tube 1. Then, the inner needle 3 is inserted into a blood vessel 4 until the tip of the guiding tube 1 is positioned within the blood vessel 4, as shown in FIG. 9. Under this condition, the inner needle 3 is withdrawn from the blood vessel 4, with the guiding tube 1 kept attached to the blood vessel 4. Further, a desired catheter 5 is inserted into the guiding tube 1 until the tip of the catheter 5 is positioned within the blood vessel 4, as shown in FIG. 10. After the catheter 5 has been attached to the blood vessel 4 as desired, it is desirable to withdraw the guiding tube 1 from the blood vessel 4 and from the catheter 5. It is sanitarily undesirable to leave the guiding tube 1 unremoved after use. Also, the guiding tube left unremoved after use hinders the operation of the catheter 5. However, the presence of an enlarged portion, such as a connector 6 of the catheter, makes it quite difficult to withdraw the guiding tube 1 from the catheter 5.

Several measures have been proposed to date for withdrawing the guiding tube 1 after use from the catheter 5. For example, it has been proposed to provide the guiding tube with a longitudinal slit to enable the guiding tube after use to be readily removed from the catheter. However, serious problems are brought about in this case. For example, the strength of the guiding tube is lowered, making it troublesome to operate the guiding tube. Also, the slit of the guiding tube is likely to expand when the catheter is inserted through the guiding tube into a blood vessel, leading to a leakage of blood. To overcome the problem, it is unavoidable to make the slit narrow with the result that removal of the guiding tube from the catheter remains difficult.

Japanese Patent Disclosure (Kokai) 56-11069 proposes another measure. Specifically, it is proposed that a guiding tube is provided with a pair of linear bodies extending along the length of the guiding tube and positioned opposite to each other in the radial direction of the guiding tube. The linear body is formed of a plastic material foreign to the material forming the main body of the guiding tube. Also, the proximal end portion of the guiding tube, which is joined to the inner needle hub, of the guiding tube is provided with a pair of slits aligned with the linear bodies. After a catheter or the like inserted through the guiding tube has been attached to a blood vessel, the proximal end portion of the guiding tube is pulled outward in opposite directions. As a result, the guiding tube after use is split into two parts along the linear bodies. Of course, the slits formed in the proximal end portion of the guiding tube facilitate the splitting. In this proposal, however, the linear body tends to be cracked during the after-treatment, such as cutting or edge-processing of the guiding tube, or during transport or the like of the product guiding tube, with the result that leakage of blood is likely to take place so as to make the guiding tube unsuitable for use.

SUMMARY OF THE INVENTION

An object of the present invention is to provide a guiding tube for rod-like medical instruments such as a catheter, which is free from accidental splitting or cracking during the after-treatment in the manufacture of the guiding tube or during a handling of the guiding tube. Another object of this invention is to provide a guiding tube which can be easily removed from, for example, a catheter after the catheter inserted through the guiding tube has been attached to a blood vessel.

According to still another aspect of the present invention, there is provided an extruder apparatus for producing a tube for guiding rod-like medical instruments into a living body, comprising a tubular body formed of synthetic resin in a hollow shape capable of positioning the rod-like medical instruments, and at least one brittle portion formed so that the splitting strength thereof is smaller than the other portion over the entire length of longitudinal direction of the tubular body or the entire length of the longitudinal direction of the tubular body except the end thereof and formed of the same material as the other portion, the extruder apparatus comprising a die including a nozzle having means for defining a resin flow passageway of annular cross-section, at least one baffle extending radially into the resin flow passageway and recessed 0 to 5 mm axially from an end of the nozzle, the height of the at least one baffle being at least ½ of a height of the resin flow passageway, whereby as the resin flow is extruded from the nozzle, the at least one baffle forms a split portion of the resin flow by substantially temporarily splitting the resin flow which is then recombined to form the brittle portion of the resin tube at the split portion of the resin flow.

BRIEF DESCRIPTION OF THE DRAWINGS

FIG. 1 is a perspective view showing a guiding tube for medical instruments according to one embodiment of the present invention;

FIG. 2 is a sectional view along line II—II of FIG. 1;

FIG. 3 is a perspective view showing the guiding tube of FIG. 1 longitudinally split into two parts along linear body from one end thereof;

FIG. 4 is a view showing a front face of an extrusion molding machine for the tube of FIG. 1;

FIG. 5 is a sectional view showing the extrusion molding machine of FIG. 4;

FIG. 6 is a view showing the front face of another embodiment of the extrusion molding machine of FIG. 4;

FIG. 7 is a sectional view of the extrusion molding machine of FIG. 6; and

DETAILED DESCRIPTION OF THE PREFERRED EMBODIMENTS

Figure 8:
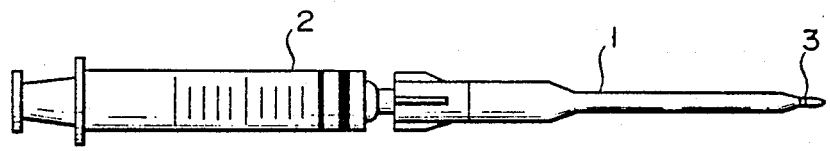
FIGS. 8 to 10 are schematic views describing prior art guiding tube for medical instruments.

As seen from FIGS. 1 to 3, guiding tube 11 for medical instruments according to one embodiment of the present invention comprises a tubular body opened at opposite ends in the shape of a hollow tube for guiding a rod-like medical instrument such as a catheter and converged at one end in contact with an inner needle, not shown, and enlarged at the other cylindrical base.

The tubular body is formed, as shown in FIG. 2, with brittle portions 12a and 12b so made at two parts of the circle of the body, i.e., at two positions opposite to each other in the radial direction along the length of the tubular body or along the entire length of the body except the opposite end that the splitting strengths are smaller than those of the other circular portion.

Brittle portions 12a and 12b of the tubular body are formed with extrusion molding machine or extruder 13 as shown, for example, in FIGS. 4 and 5. Molding machine 13 comprises a pair of baffles 15a and 15b so positioned oppositely to each other on the inner peripheral surface of inner die 16 and projected oppositely from the inner peripheral surface of die 16 in the radial direction in annular passageway 18 in the vicinity of a nozzle of annular die 14 that the molded parts of the tubular body passing baffles 15a and 15b naturally become brittle portions 12a and 12b.

Baffles 15a and 15b may be determined at the positions and in the heights properly in relation to the type and the mixture of synthetic resin to be used. When distance L between the end positions of baffles 15a and 15b and the end of die 14 is 0 to 5 mm and distance h between the upper ends of baffles 15a, 15b and the inner wall of die 17 is set to h : H =0 to ½: 1, preferably 0 to 1/5 : 1 to the interval H of resin passageway 18, brittle portions 12a, 12b having desired splitting strength are provided.

When the tubular body of the guiding tube for the medical instrument is molded by the extruder provided with baffles 15a and 15b near the nozzle of die 14 under the above-mentioned conditions, softened resin guided into die 14 by a screw, not shown, is fed in die 14 temporarily substantially split state by baffles 15a, 15b, is again bonded to each other in the nozzle or in the vicinity of the nozzle of die 14 to be molded in a tubular shape.

The tubular body thus molded is formed substantially smoothly at a glance in a continuous circular shape, but is formed with welding lines, i.e., brittle portions 12a, 12b in the portions passing baffles 15a, 15b. Since brittle portions 12a, 12b remarkably decrease in bonding strength between synthetic resins of other circular portion, portions 12a, 12b are readily broken by applying an external stress thereto, and are, for example, readily split as shown in FIG. 3.

The splitting strength of brittle portions 12a, 12b may be regulated by adjusting the positions, the heights and the widths (lengths or thicknesses) of baffles 15a, 15b or arbitrarily adjusting the mixture of two or more resins.

Thermoplastic resins such as polypropylene, fluorinated plastics, chlorinated polyethylene, blend polymer of polyolefin resin and ethylene/vinyl acetate copolymer are used properly selectively as the material of the tubular body of the guiding tube for the medical instruments.

The case that the extruder in which baffles 15a, 15b are projected on the inner die has been used has been described as shown in FIGS. 5 and 6. However, the present invention is not limited to the particular embodiment. Various other changes and modifications may be made within the spirit and scope of the present invention. In the embodiment described above, other arbitrary molding means may be employed. For example, as shown in FIGS. 6 and 7, the same baffles 15a, 15b as those which have been described with reference to FIGS. 4 and 5 may be positioned oppositely to the annular die 14 (in which symbols designate all the same as those in FIGS. 4 and 5). Further, though not shown, similar baffles may be projected oppositely to annular and inner dies. In any case, the positions (L), the heights (h) and the sizes of the baffles may be regulated and selected similarly to the case of FIGS. 4 and 5.

A method of using the guiding tube for the medical instrument of the present invention will be described.

Figure 9:
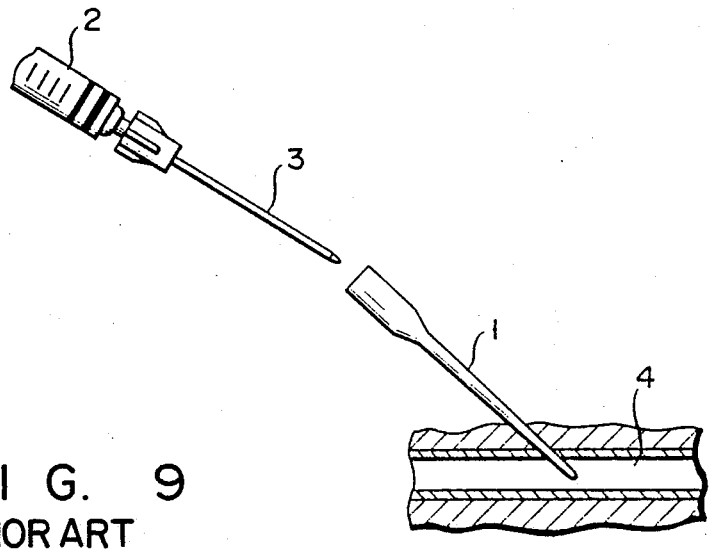
Figure 10:
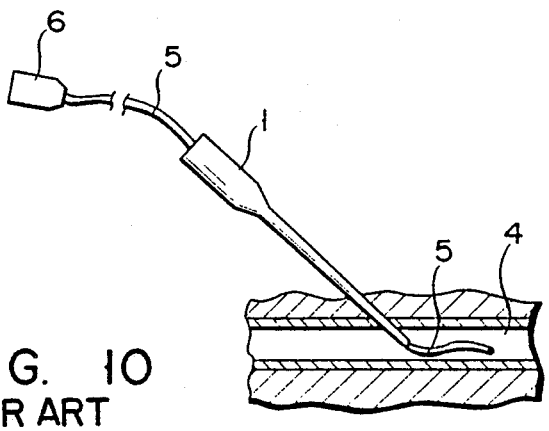

Guiding tube 11 of the present invention is, for example, mounted to syringe 2 as shown in FIG. 8 with respect to guiding tube 1, and is then positioned together with the inner needle of syringe within a blood vessel, as shown in FIG. 9. Under this condition, inner needle 3 is withdrawn from the blood vessel, with guiding tube 11 kept attached to blood vessel 4. Then, a catheter is inserted into guiding tube 11 so that catheter is positioned within the blood vessel.

Then, in withdrawing guiding tube 11 after use from the catheter, an external stress is applied to guiding tube 11 as shown in FIG. 3 to cut the base ends of brittle portions 12a, 12b, and tube 11 is split through the base ends of brittle portions 12a, 12b. Then, guiding tube 11 can be readily withdrawn from catheter 5.

In the embodiments described above, the catheter has been guided as the guiding tube for the medical instruments. However, the present invention is not limited to the catheter, but may be applied to the case that all types of rod-shaped medical instruments are positioned within a living body.

The above-mentioned brittle portions to be split are not limited to the two linear bodies as in the embodiments described above, but may be provided with one or three or more linear bodies of the brittle portions.

The guiding tube for the medical instrument according to the present invention as described above is not necessarily provided with the linear bodies formed of a synthetic resin foreign to the material forming the tubular body of the guiding tube as the conventional art but is molded of a sole plastic composition. Thus, the linear body can avoid to be unintentionally cracked during the after-treatment, such as cutting or edge-processing of the guiding tube, the guiding tube can be manufactured readily, leading to a low manufacturing cost of the guiding tube.

EXAMPLE 1

A pair of baffles having 22 mm long and 0.5 wide were provided, as shown in FIG. 7, in contact with the inner wall of the inner die at the annular die of an extruder so that the tip thereof was disposed at the position of 0.5 mm before the nozzle of the die (i.e., "L"=0.5 mm in FIG. 7). Then, a guiding tube fitting a 16G inner needle was prepared by polypropylene. Even when the tip of the guiding tube was processed in contact with the 16G inner needle, the guiding tube was found to be free of problems such as cracking of the tip portion. Also, the pin portion of the guiding tube was free from roughening, cracking, etc. when the guiding tube was stuck in a blood vessel of a dog together with the inner needle. Further, the linear body was readily peeled from the tubular body in removing the guiding tube.

COMPARISON EXAMPLE 1

A catheter guiding tube was prepared by extrusion molding similarly to the Example 1 except that the similar baffles to those in the Example 1 were disposed at a position of 6 mm before the nozzle of the die. However, in this case, the guiding tube was not substantially molded with brittle portions and could not be split.

COMPARISON EXAMPLE 2

Similar baffles to those of the Example 1 were projected on the inner wall of the annular die having 5 mm of inner diameter. However, in this case, the heights of the baffles were separated 0.6 mm from the peripheral surface of the inner die having 4 mm of outer diameter, and the ends of the baffles were positioned 0.5 mm before the nozzle of the die. When a catheter guiding tube was molded similarly to the Example by this extruder, a brittle portion was not substantially molded and the guiding tube could not be split.

What is claimed is:

1. An extruder for producing a synthetic resin tube for guiding rod-like medical instruments into a living body, said tube having a tubular body with a circular hollow transverse cross section of a uniform thickness and being capable of positioning the rod-like medical instruments, and having at least one brittle portion and another portion, said at least one brittle portion being formed so that the splitting strength thereof is smaller than the splitting strength of said other portion over at least the entire length of the tubular body except the end thereof, said at least one brittle portion being formed of the same material as the other portion, said extruder comprising:

a die including a nozzle having means for defining a resin flow passageway of annular cross-section;

at least one baffle extending radially into said resin flow passageway and recessed 0 to 5 mm axially from an end of said nozzle, the height of the at least one baffle being at least ½ of a height of said resin flow passageway;

whereby as the resin flow is extruded from the nozzle, the at least one baffle forms a split portion of the resin flow by substantially temporarily splitting the resin flow which is then recombined to form the brittle portion of the resin tube at the split portion of the resin flow.

2. An extruder according to claim 1, wherein the height of the at least one baffle is at a ratio of 0 to 1/5 to a height of 1 of said flow passageway.

* * * * *